United States Patent [19]

Shimizu et al.

[11] Patent Number: 4,807,639
[45] Date of Patent: Feb. 28, 1989

[54] PULSE DETECTION APPARATUS

[75] Inventors: Atsuko Shimizu; Hiroshi Fujii; Shinichi Ohki, all of Tokyo, Japan

[73] Assignee: Casio Computer Co., Ltd., Tokyo, Japan

[21] Appl. No.: 901,783

[22] Filed: Aug. 28, 1986

[30] Foreign Application Priority Data

Aug. 31, 1985 [JP] Japan .................................. 60-192632
Aug. 31, 1985 [JP] Japan .................................. 60-192633

[51] Int. Cl.$^4$ ............................................. A61B 5/02
[52] U.S. Cl. ........................................ 128/690; 128/706
[58] Field of Search ....................... 128/690, 707, 706

[56] References Cited

U.S. PATENT DOCUMENTS

| | | | |
|---|---|---|---|
| 3,937,004 | 2/1976 | Natori et al. | 128/690 |
| 3,978,849 | 9/1976 | Geneen | 128/690 |
| 4,009,708 | 3/1977 | Fay, Jr. | 128/690 |
| 4,086,916 | 5/1978 | Freeman et al. | 128/690 |
| 4,101,071 | 7/1978 | Brejnik et al. | 128/690 |
| 4,202,350 | 5/1980 | Walton | 128/690 |
| 4,278,095 | 7/1981 | Lapeyre | 128/707 |
| 4,281,663 | 8/1981 | Pringle | 128/707 |
| 4,305,401 | 12/1981 | Reissmueller et al. | 128/690 |
| 4,425,921 | 1/1984 | Fujisaki et al. | 128/690 |
| 4,450,843 | 5/1984 | Barney et al. | 128/690 |
| 4,489,731 | 12/1984 | Baumberg | 128/690 |
| 4,566,461 | 1/1986 | Lubell et al. | 128/689 |

Primary Examiner—Francis Jaworski
Assistant Examiner—George Manuel
Attorney, Agent, or Firm—Frishauf, Holtz, Goodman & Woodward

[57] ABSTRACT

A pulse detection apparatus includes a memory for storing the normal pulse count of a user. After taking some exercise such as jogging, the percentage of the pulse count, detected by a pulse sensor, with respect to the normal pulse count, is calculated, and the results are displayed, to allow the user to determine the recovery rate of his physical strength.

21 Claims, 19 Drawing Sheets

F I G. 16
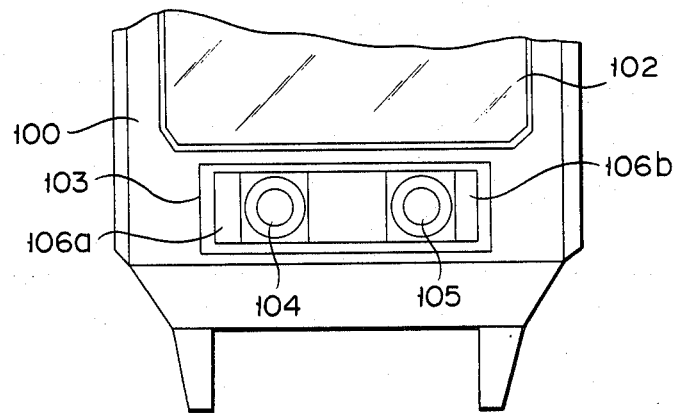
F I G. 17
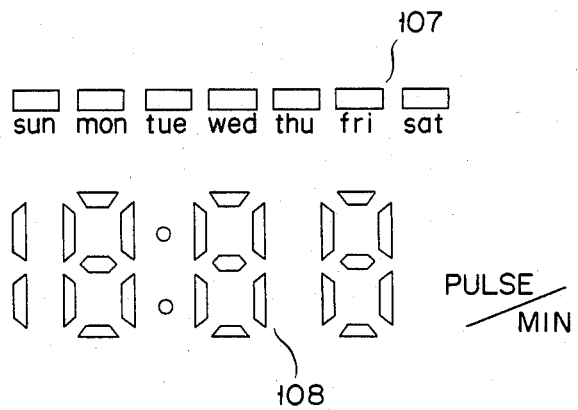

F I G. 19A 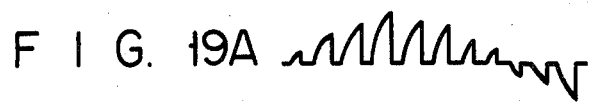
F I G. 19B 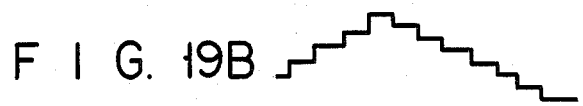
F I G. 19C 
F I G. 19D 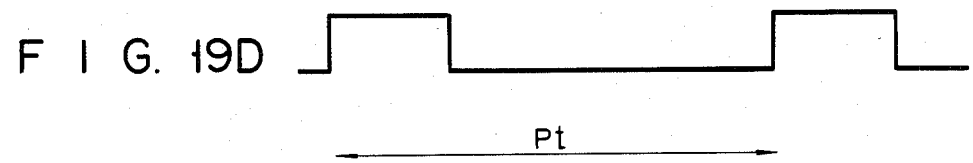
F I G. 20
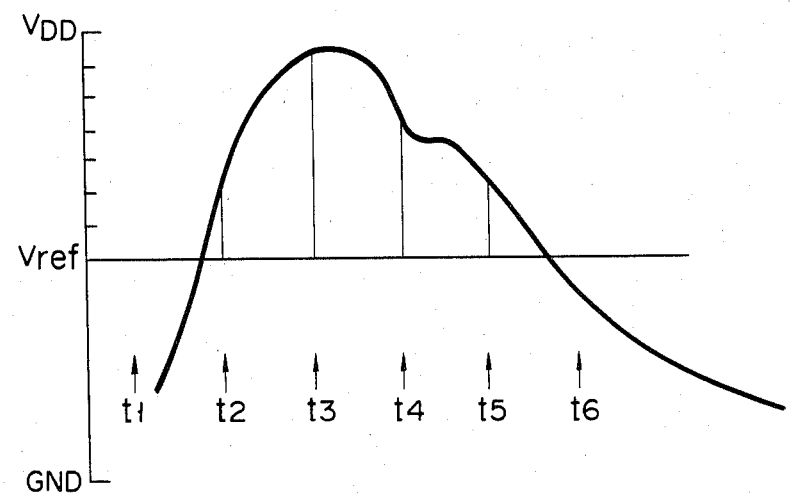

F I G. 27A 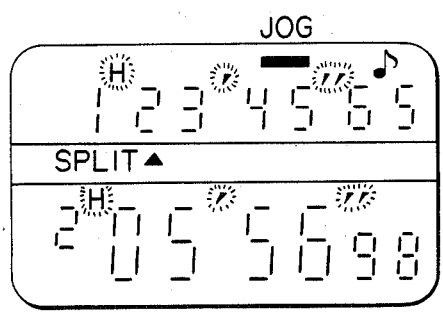
F I G. 27B 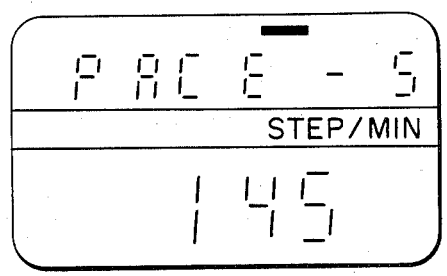
F I G. 27C 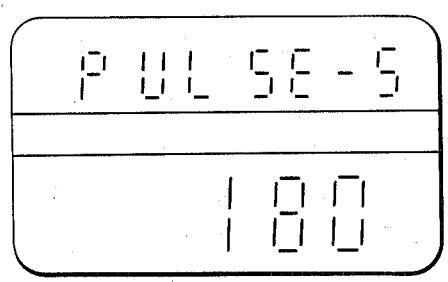
F I G. 27D 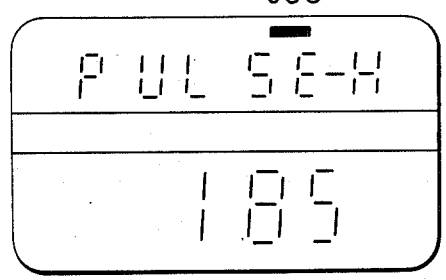

PULSE DETECTION APPARATUS

BACKGROUND OF THE INVENTION

The present invention relates to a pulse detection apparatus incorporated in a jogging watch, a stopwatch, or a wristwatch to detect an increase in physical strength as a result of jogging or any other exercise, through detecting the number of pluse (heartbeats).

A conventional pulse counter for electronically counting the number of pulses and displaying the count is well known. For example, U.S. Pat. No. 4,009,708 describes a wristwatch type pulse counter capable of counting the number of pulses per minute.

U.S. Pat. No. 4,101,071 describes an apparatus for calculating a calorie burn total according to the number of pulses and the length of exercise time.

An assembly obtained by incorporating a pulse sensor in an electronic wristwatch is also known. For example, U.S. Pat. No. 3,937,004 describes a technique for incorporating a pulse sensor in a wristwatch. U.S. Pat. No. 4,086,916 describes a technique for incorporating a pulse sensor in a wristwatch band.

In addition, U.S. Pat. No. 3,978,849 describes an apparatus for displaying an optimal exercise amount as well as the number of pulses, or signalling to the user that the number of pulses is too high.

Although the conventional apparatuses can detect the number of pulses, the exercise amount, dangerous physical condition, and the like, they cannot detect the level of increase in physical strength. More specifically, people do exercise such as jogging to maintain and develop fitness. Before exercise, the physical strength of individual persons varies. In addition, physical strength after taking exercise varies according to the degree of difficulty and duration of the exercise, and the physical fitness of each person. Therefore, no conventional apparatus can provide a criterion for detecting an increase in physical strength, thereby resulting in inconvenience.

SUMMARY OF THE INVENTION

The present invention has been made in consideration of the above situation, and has as its object to provide a pulse detection apparatus for accurately and easily detecting the degree of increase in physical strength upon taking exercise, through detecting the number of pulses.

In order to achieve the above object of the present invention, there is provided a pulse detection apparatus comprising key input means for input of a pulse count per unit time, storage means for storing the pulse count input at said key input means, a pulse sensor for detecting an actual pulse, pulse measuring means for measuring the pulse count per unit time, according to a detection output signal from said pulse sensor, operating means for performing a predetermined arithmetic operation using at least the pulse count measured by said pulse measuring means and the pulse count stored in said storage means, and for producing operation data on the basis of the pulse count stored in said storage means, and display means for displaying the operation data calculated by said operating means.

With the above arrangement, the pulse detection apparatus of the present invention has an effect for detecting the degree of an increase in physical strength upon taking exercise. The increased number of pulses after a person takes a predetermined exercise can be generally reduced to the normal number of pulses within a shorter period of time as his physical strength increases. According to the present invention, the number of pulses is measured to detect the recovery rate or the recovery time, and the recovery rate or time is displayed to allow the user to easily determine the degree of increase in his physical strength.

BRIEF DESCRIPTION OF THE DRAWINGS

FIG. 16 is a schematic view showing part of the outer appearance of a watch case of a jogging watch according to still another embodiment of the present invention;

FIG. 17 is a detailed view of the display unit used in FIG. 16;

FIGS. 19A to 19D are timing charts showing the waveforms of the outputs from the circuit in FIG. 18;

FIGS. 20 and 22 are respectively graphs showing output voltages of the circuit in FIG. 18;

FIGS. 21A to 21F and FIGS. 23A to 23F are views showing display states of the output voltages in FIG. 19;

FIGS. 27A to 27D are respectively views showing the display states of the display unit in FIG. 24;

DETAILED DESCRIPTION OF THE PREFERRED EMBODIMENTS

An embodiment of the present invention will now be described in detail with reference to the accompanying drawings.

Figure 1:
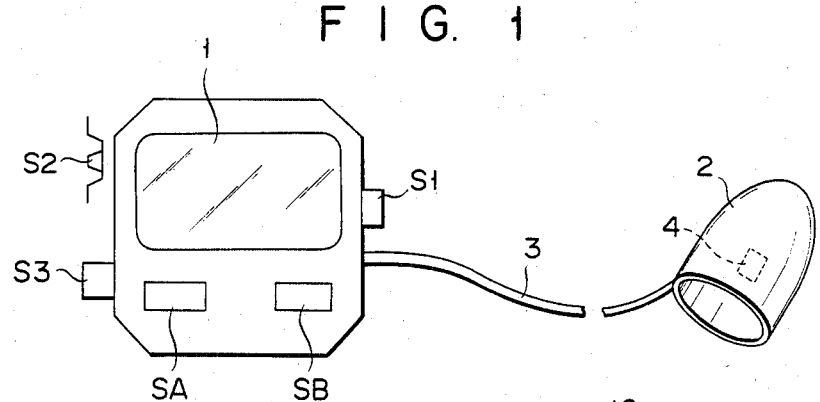
FIG. 1 is a schematic view showing the outer appearance of a jogging watch with a built-in pulse detection apparatus according to the present invention.
Figure 2:
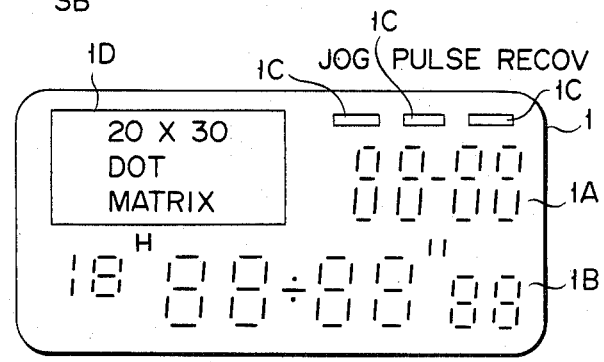
FIG. 2 is a plan view showing the detailed arrangement of a display unit in the jogging watch in FIG. 1.
Figure 3:
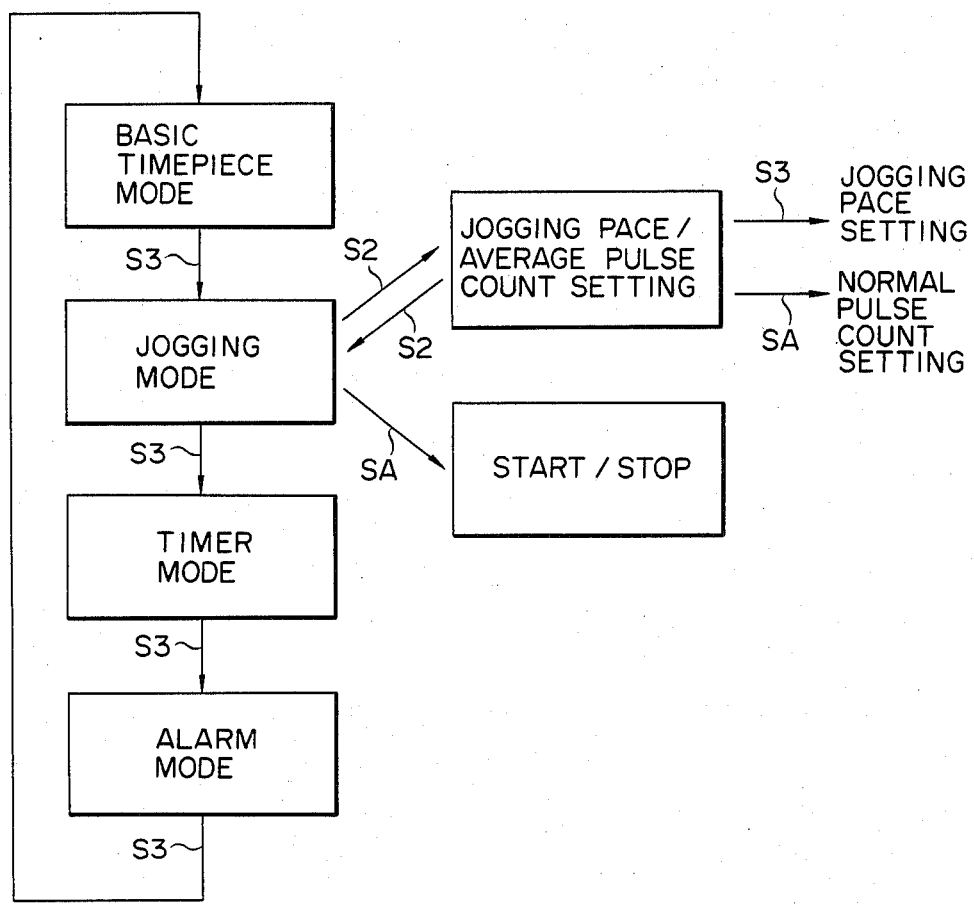
FIG. 3 is a flow chart for explaining changes in display modes upon switching operations.

FIG. 1 is a plan view showing the outer appearance of a jogging watch with a built-in pulse detection apparatus according to the present invention. Display unit 1 is arranged on the upper surface of the watch case. Unit 1 comprises liquid crystal display elements. As shown in FIG. 2, unit 1 includes upper digital display section 1A for digitally displaying the date, and lower digital display section 1B for displaying the time (hour, minute, second, and second/100). Unit 1 also includes mode indicators 1C showing jogging mode name "JOG", pulse count mode name "PULSE", and recovery time count mode name "RECOV" for indicating the time required for the user to recover to the preset normal number of pulses after he has stopped jogging. These names are printed in positions corresponding to indicators 1C. Display unit 1 further includes display section 1D of a 20×30 dot matrix. As shown in FIG. 1, pushbutton switches SA, SB, S1, S2, and S3 are arranged on the upper surface and the sides of the watch case. These switches function as shown in FIG. 3. Switch S3 serves as a mode selection switch for cyclically setting a basic timepiece mode, a jogging mode, a timer mode, and an alarm mode. Switch S2 serves as a set mode selection switch for selecting jogging pace setting or normal pulse count setting. Upon operation of switch S2, the currently set mode is cancelled, and the previous jogging mode is restored. Although omitted in FIG. 3, upon operation of switch S2 in the basic timepiece mode, the time correction mode is set; upon operation of switch S2 in the alarm mode, the alarm setting mode is initiated. Upon operation of switch S3 in pace or normal pulse count setting, a desired pace count (number of steps/minute) can be set according to the number of operations of switch S3. In addition, when switch SA is operated, a desired normal pulse count falling within the range of 30 pulses to 100 pulses can be set according to the number of operations of switch SA. The desired normal pulse count is then stored in the P register in RAM 16 (to be described later). Switch SA serves as a start/stop switch in the jogging mode. When jogging begins upon operation of switch SA, alarm tones are generated at the pace set with switch S3. Switch SB serves as a split/reset switch (not shown). U.S. Pat. No. 4,510,485 describes a technique for setting a pace count and generating pace tones upon operation of the start/stop switch.

Referring to FIG. 1, fingerstall 2 is detachably connected to one side of the watch case, through cord 3. Pulse sensor 4 is arranged inside fingerstall 2. Sensor 4 consists of a light-emitting element such as an LED, and a light-receiving element such as a phototransistor. Light from the light-emitting element is emitted onto a finger, and light reflected by the finger is incident on the light-receiving element. A change in the amount of blood flowing, caused by pulses, is detected as a change in the amount of received light. The number of pulses is measured according to the resultant photoelectric pulse wave. Pulse detection will be described in more detail later.

The arrangement of the jogging watch circuit will be described with reference to FIG. 4. The jogging watch is operated according to a microprogram control system capable of 8-bit parallel processing. A 32.768-kHz clock signal normally generated by oscillator 11 is frequency-divided by frequency divider 12. The frequency-divided signal is supplied to timing signal generator 13. Generator 13 supplies various timing signals to ROM (Read Only Memory) 14 and other circuits to be described later.

ROM 14 stores a microprogram for controlling all operations of the jogging watch and outputs parallel microinstructions OP, DO, and NA. Microinstruction OP is input to instruction decoder 15. Decoder 15 decodes microinstruction OP and supplies it as a read/write instruction to input terminal R/W of RAM (Random Access Memory) 16 and as an operation instruction to input terminal S of operation unit 17. Decoded microinstruction OP is also supplied as an operation instruction to input terminal S of pacemaker circuit 18. Circuit 18 supplies a signal to address controller 19, to generate pacemaker tones. Microinstruction DO is supplied as address data to input terminal Addr of RAM 16 through a data bus and as numeric data to input terminal DI2 of operation unit 17. Microinstruction DO is also input to pacemaker circuit 18 and address controller 19. Microinstruction NA is next-address data input to controller 19. Address data output from controller 19 is input to input terminal Addr of ROM 14. Decoder 15 outputs an alarm tone generation instruction and a stop instruction which are respectively supplied to input terminals S and R of SR flip-flop (SR-FF) 20, thereby setting and resetting SR-FF 20. A Q output from SR-FF 20 is supplied as a drive signal to alarm circuit 21, to cause alarm tone generation section (i.e., a loudspeaker or a piezoelectric element) 22 to produce alarm tones.

Although the arrangement of RAM 16 will be described in detail later, RAM 16 has an input data register, an operation register, and the like, and is used for timepiece processing, key input processing, arithmetic processing, and jogging processing. RAM 16 is read/write accessed under the control of instruction decoder 15. Data read out from output terminal DO of RAM 16 is supplied to input terminal DI1 of operation unit 17 and pacemaker circuit 18, and is displayed on display unit 1 through display controller (consisting of a decoder and a driver) 25. Operation unit 17 performs various arithmetic operations in response to operation instructions from instruction decoder 15. Operation result data from output terminal DO of operation unit 17 is supplied to input terminal DI of RAM 16 and stored therein. Operation unit 17 also outputs a signal representing the presence/absence of the operation result data, and a signal representing the presence/absence of a carry signal in the judging sequence. These signals are supplied to address controller 19, to update the address of ROM 14, so that timepiece processing is executed by interruption for every 1/32 second. An output from pulse detection control circuit 23 for converting a photoelectric pulse wave detected by pulse sensor 4 to a signal representing the corresponding number of pulses, is input to input terminal DI3 of unit 17. A key code output upon operation of a switch is supplied from input unit 24 to input terminal DI2 of unit 17.

Figure 5:
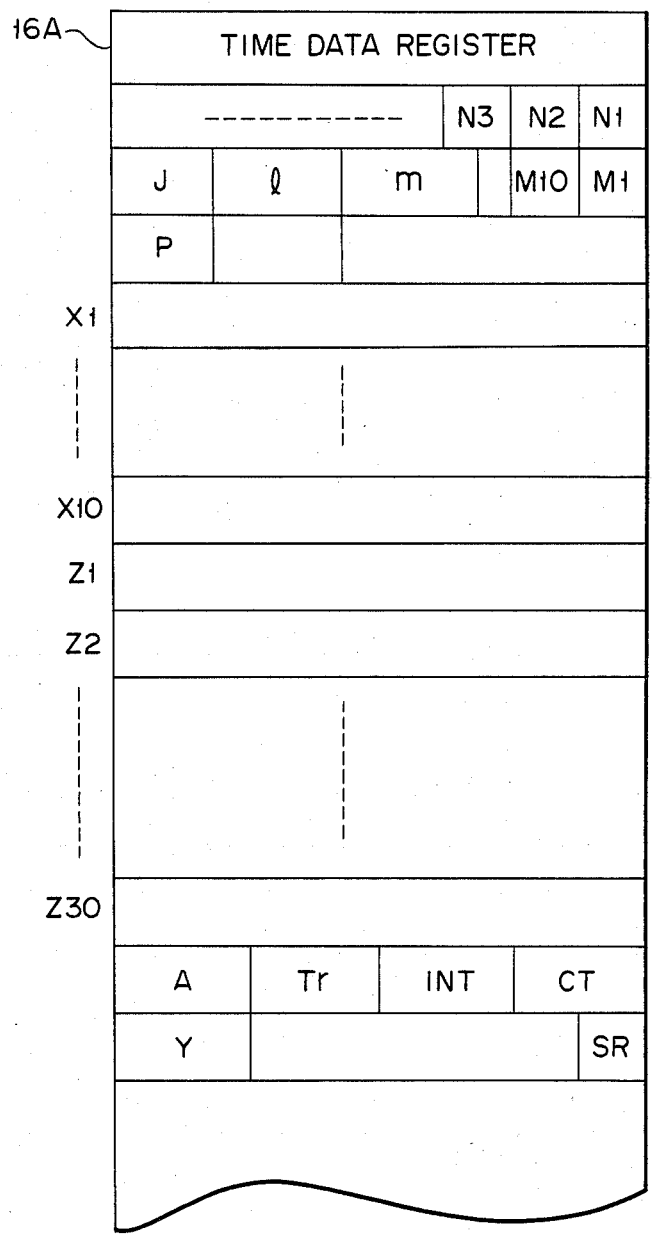
FIG. 5 is a memory map showing the detailed allocation of the memory area in RAM 16 in FIG. 4.

FIG. 5 shows the memory map of the memory area of RAM 16. Referring to FIG. 5, reference numeral 16A denotes a register for storing current time data. Reference symbols N1, N2, and N3 denote registers for storing time periods after the start of jogging; and J, a register for storing the end of jogging. Reference symbols M1 and M10 denote registers for respectively storing one minute and 10 minutes after the start of jogging; and X1 to X10, registers for storing pulse counts, respectively. The 1 register designates addresses of registers X1 to X10. Reference symbols Z1 to Z30 denote registers for storing average counts of 10 pulse detection cycles; and m, a register for designating the addresses of registers Z1 to Z30.

Reference symbol P denotes a register for storing the jogging pace count; and A, a register for storing the normal pulse count.

Reference symbol Tr denotes a register for counting a period after the end of jogging; INT, a 5-second timer register; Y, a register for storing a pulse count for every five seconds; CT, a binary register; and SR, a register for storing an alarm tone generation flag.

The overall operation of the circuit described above will now be decribed with reference to FIG. 6. In step T1, the circuit is held in the waiting state (HALT) until a timepiece or key processing request is generated. If a timepiece timing is obtained, the flow advances to step T2. The timepiece processing program is accessed and timepiece processing is started. Basic timepiece data stored in timepiece storage register 16A in the first line of RAM 16 is added to predetermined unit data, to obtain current time. The current time data is transferred to register 16A in RAM 16, to update the time to the current time. In the next step T3, the content of the J register in RAM 16 is checked. The J register stores the jogging mode flag. During jogging measurement, J=1 is set. In this case, jogging processing (to be described in detail later) is performed, in step T4. However, if the user does not jog, the flow advances to step T5 to determine whether J=2 is set. If YES in step T5, recovery time measurement is performed, in step T6. When jogging processing (step T4) and recovery time measurement (step T6) are completed, display processing is performed in step T7, and the flow returns to step T1.

Upon operation of any switch, a corresponding key processing program is accessed, and key processing thereof is performed, in step T8. The processed results are displayed in step T7, and the flow returns to step T1. When a jogging pace or normal pulse count is set in the jogging mode, switch S2 is operated, to select the setting mode. If the pace count is set, switch S3 is operated; and if the normal pulse count is set, switch SA is operated. As a result of key processing in step T8, a desired jogging pace count is set in the P register, according to the number of operations of switch S3. A desired normal pulse count of the user is set in the A register, according to the number of operations of switch SA. When various necessary data are registered prior to jogging, the user operates switch S1, to change to the jogging mode. Thereafter, the user operates switch SA when he starts jogging. Upon operation of switch SA, a jogging mode flag "1" is set in the J register in RAM 16. Upon second operation of switch SA, the jogging mode is interrupted and "2" is set in the J register.

Figure 6:
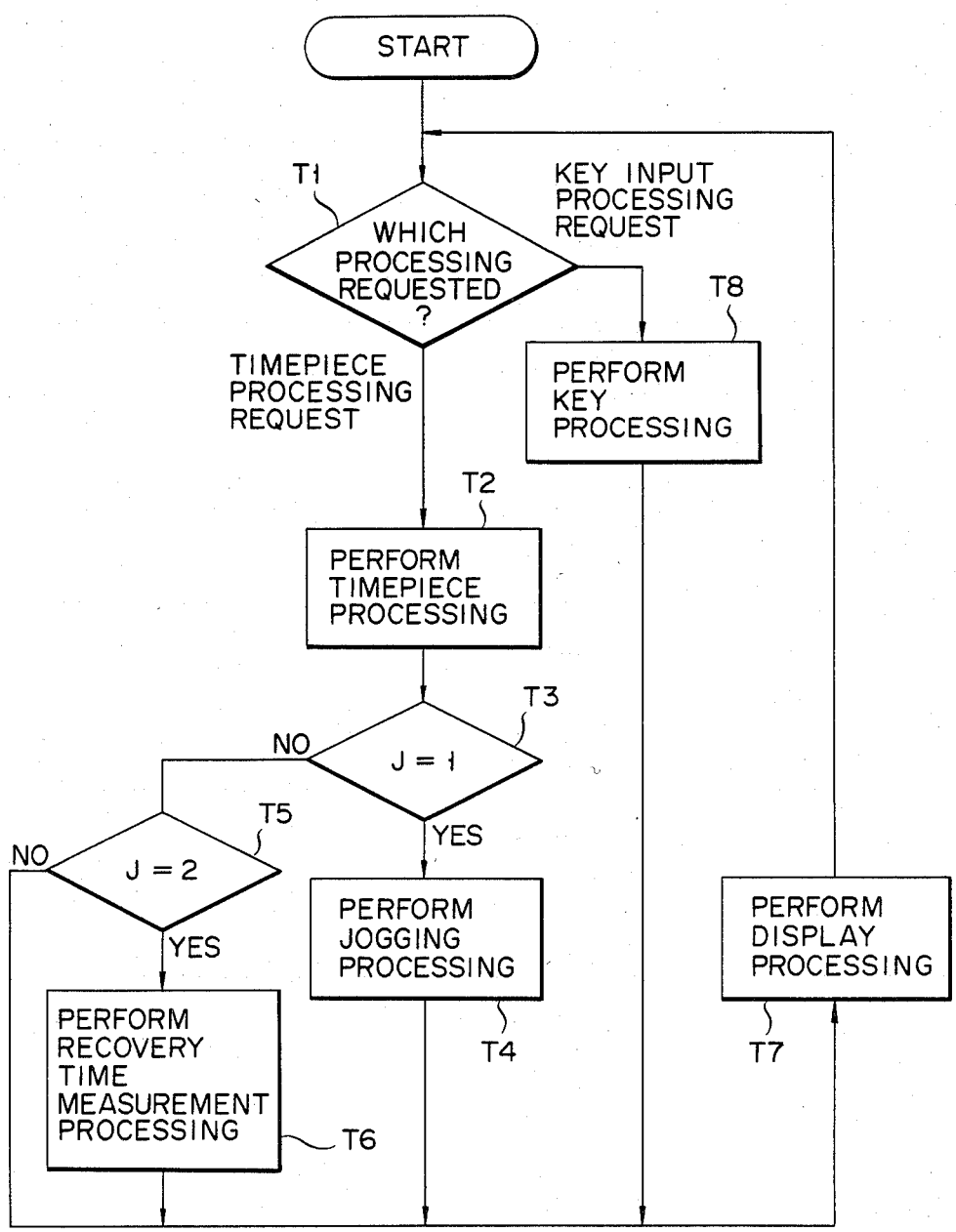
FIG. 6 is a flow chart showing the general operation of the jogging watch in FIG. 1.
Figure 7:
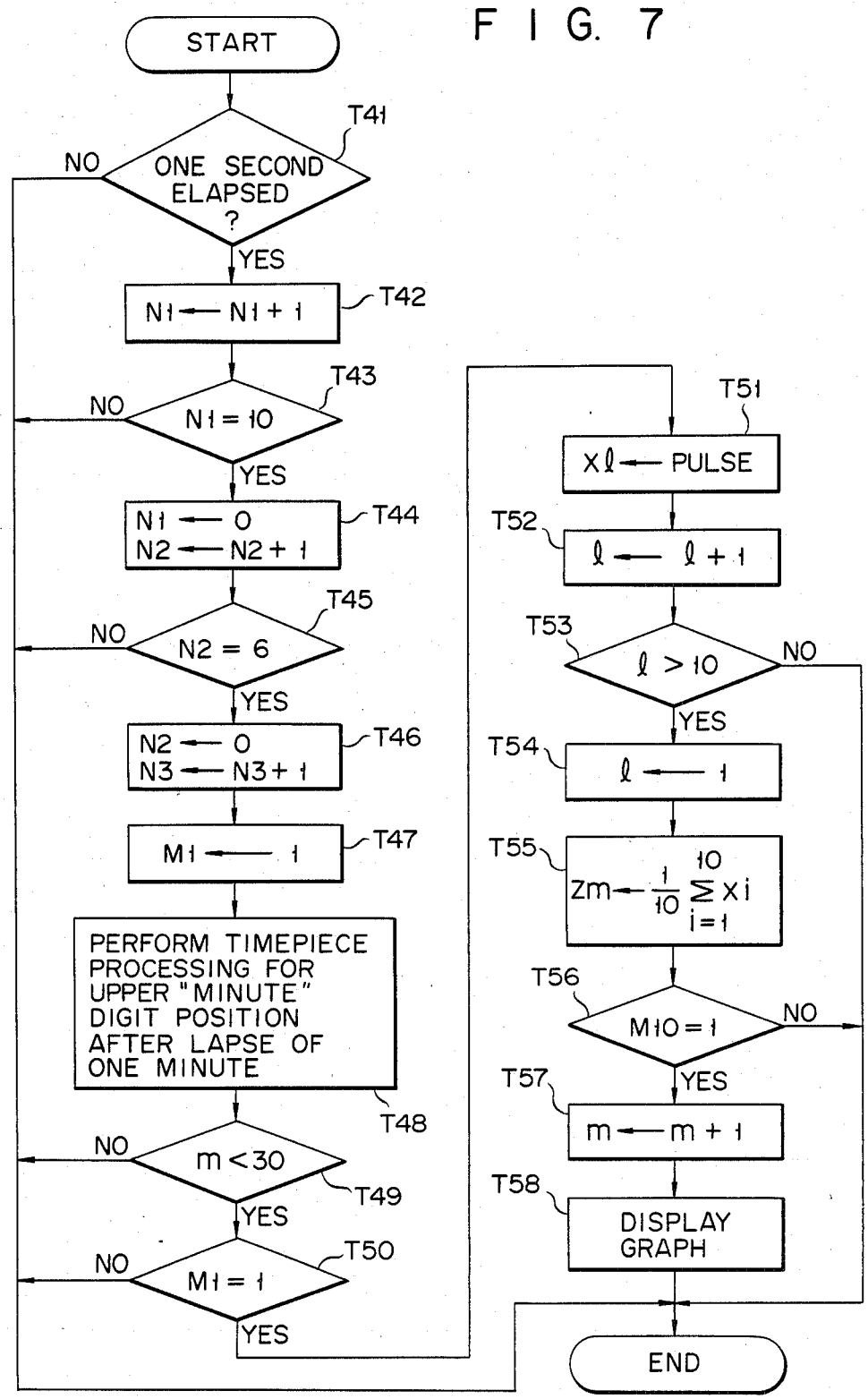
FIG. 7 is a flow chart showing the detailed operation in step T4 in FIG. 6.

FIG. 7 is a flow chart for explaining detailed operations of jogging processing (step T4) in FIG. 6. In step T41, a check is made as to whether a one-second signal after the start of jogging is present. If the one-second signal is determined to have been output, the content of the N1 register (i.e., the jogging measurement register for measuring jogging time in units of seconds) in RAM 16 is incremented in incrementation processing, in step T42. As a result, if the value of the N1 register is "10", i.e., if the current timing is discriminated as each 10th second timing after the start of jogging, the flow advances to step T44. In step T44, the content of the N1 register is cleared, and at the same time the N2 register (the jogging measurement register for measuring jogging time for every 10 seconds) in RAM 16 is incremented by one. Whether or not each one minute has elapsed after the start of jogging, is determined in step T45. In other words, it is determined whether the count of the N2 register is "6". If YES in step T45, the content of the N2 register is cleared and the content of the N3 register (the jogging measurement register for measuring each one minute of the jogging time) in RAM 16 is incremented by one, in step T46. In step T47, a one-minute lapse flag "1" is set in the M1 register in RAM 16, so as to indicate the timing representing the lapse of each one minute after the start of jogging. This logic flag "1" in the M1 register is used to execute pulse measurement (to be described later). Upon start of jogging, the N1, N2, and N3 registers are updated to sequentially measure time values for one-second, 10-second, and 1-minute digit positions. In step T48, the time measurement for the upper "minute" digit position after the lapse of one minute, is detected in the same manner as described above.

The pulse count operation, upon start of jogging, is performed in the following manner:

In step T49, it is determined whether the value of the m register in RAM 16 is "30". If NO in step T49, in step T50, whether a one-minute lapse timing is obtained is determined according to whether the content of the M1 register includes the logic flag "1". The pulse measuring operation is performed in step T51 at the timing representing the lapse of each one minute after start of jogging. The measured pulse count is stored in the X1 register among the X1 to X10 registers in RAM 16, in response to the value of the l register. The X1 to X10 registers are for storing pulse counts per minute. Incrementation processing is performed in step T52, to increment the value of the l register by one. In step T53, it is determined whether the value of the l register exceeds "10". If ten one-minute pulse counts are detected, the value of the l register exceeds "10". Initialization processing is then performed in step T54 to transfer "1" to the l register. The one-minute pulse counts are sequentially stored in the X1 to X10 registers. The ten one-minute pulse counts are subjected to an operation $$(1/10) \sum_{i=1}^{10} Xi,$$

in step T55, thereby obtaining an average pulse count for 10 minutes. The average pulse count is stored in the Zm register among the Z1 to Z30 registers, in response to the value of the m register. The Z1 to Z30 registers are 10-minute average pulse count storage registers. In step T56, the content of the M10 register in RAM 16 is checked. The M10 register stores a 10-minute lapse flag. Whenever 10 minutes have elapsed, incrementation processing is performed, in step T57, to increment the value of the register by one. The contents of the Z1 to Z30 registers are displayed as a graph in dot matrix display section 1C, in step T58. This operation is repeated until the count of the m register reaches "30". A maximum of thirty 10-minute average pulse counts (for a period of five hours) are sequentially stored in the Z1 to Z30 registers, and the contents thereof are displayed as a graph.

Figure 9A:
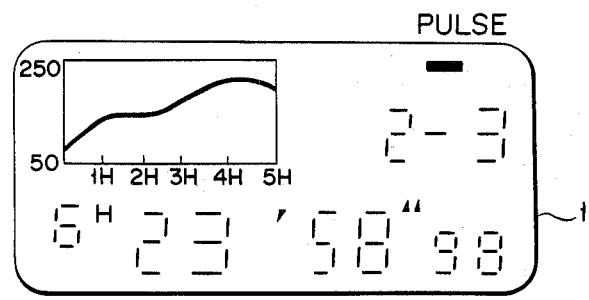
FIGS. 9A and 9B are plan views of the display unit in FIG. 2, showing different display states, respectively.

FIG. 9A shows a displayed graph. Every time the pulse count is measured, the display state is set in the pulse measurement mode. The date data of jogging is displayed in digital display section 1A. Time data of the pulse count measurement is displayed in digital display section 1B. A graph showing the 30 average 10-minute pulse counts is displayed in display section 1D. Since changes in pulse counts during jogging can be displayed as a graph, the user can check changes in the graph, to obtain subsequent pacemaking criteria, thereby effectively improving his physical strength.

Figure 9B:
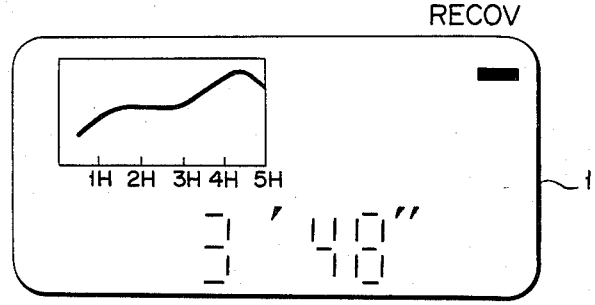
Figure 8:
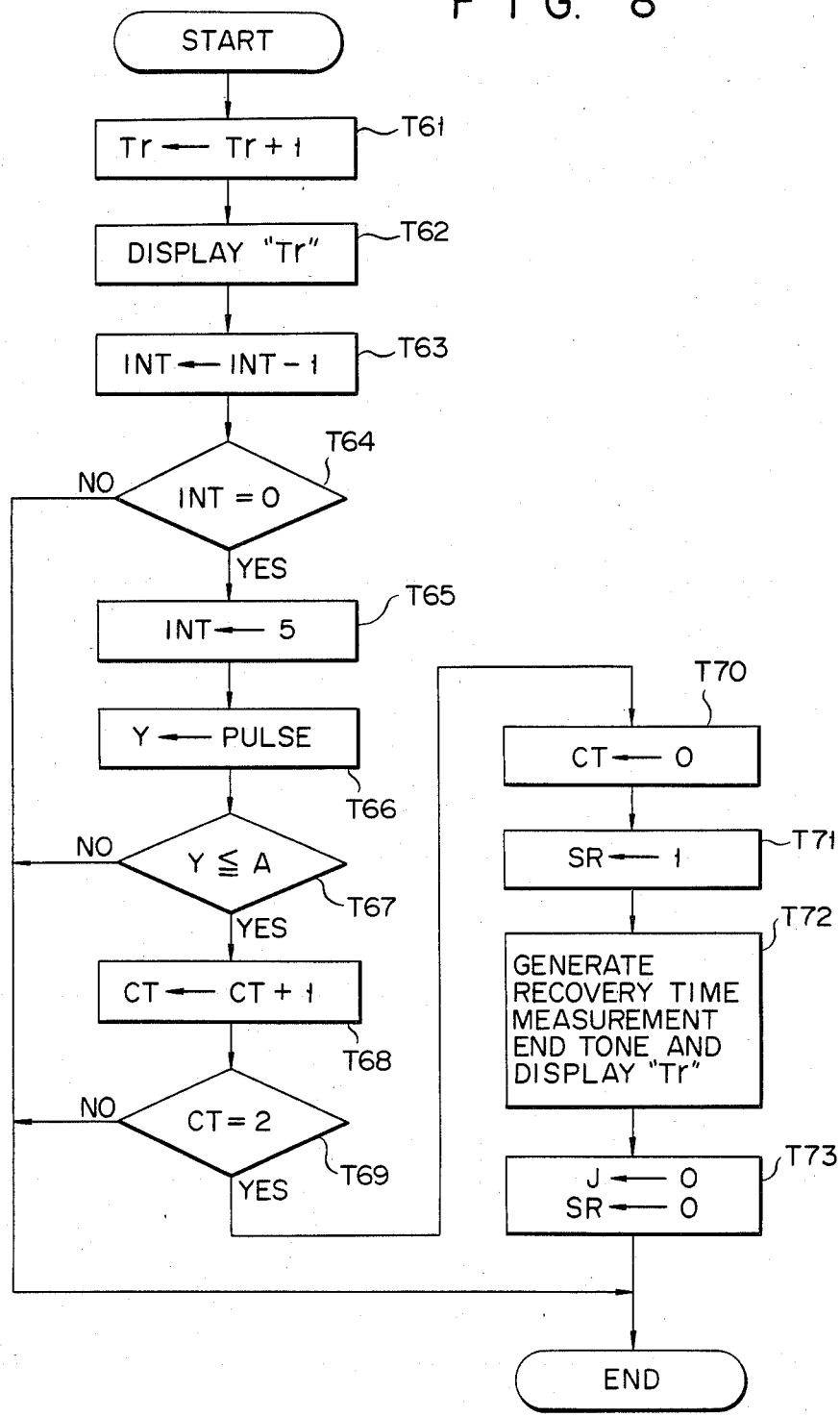
FIG. 8 is a flow chart showing the detailed operation in step T6 in FIG. 6.

FIG. 8 is a flow chart of recovery time measurement (step T6) in FIG. 6. This flow is started by interrupting jogging. In step T61, the count of the Tr counter in RAM 16 is incremented by one. The Tr counter is a recovery time measuring counter for measuring the time required for recovering to normal pulse count after jogging. The recovery time is displayed in display section 1B, in step T62. The count of the INT counter in RAM 16 is decremented by one, in step T63. The INT counter is for counting a pulse count measuring interval for every five seconds after the end of jogging. In step T65, it is determined whether the count of the INT counter has reached zero. If YES in step T65, the initial count value "5 seconds" is set in the INT counter. After a lapse of 5 seconds, the pulse count is measured, in step T66, and the count value is transferred to the Y register in RAM 16. In step T67, the count value in the Y register is compared with the normal count value in the A register in RAM 16. If the measured value is smaller than the normal pulse count, the flow advances from step T67 to step T68, in which the count of the CT counter in RAM 16 is incremented by one. The CT counter counts the number of events that the measured value is smaller than the normal pulse count in order to find that such an event happens twice succesively. In step T69, it is determined whether the value of the CT counter is "2". If the values measured for every five seconds after jogging are smaller, twice consecutively, than the normal pulse count, this is detected in step T69. The flow advances to step T70, and the count of the CT counter is cleared. The recovery time measurement end tone flag "1" is set in the SR register in RAM 16, in step T71. In step T72, the recovery time measurement end tones are generated at alarm tone generation section 22, to signal to the user, by use of a tone, the end of recovery time measurement. At the same time, the content of the Tr register is displayed. Thereafter, the SR and J registers are cleared, in step T73. The Tr counter measures as the recovery time, a period after which the pulse count measured for every five seconds is smaller, twice consecutively, than the normal pulse count. As a result, the recovery time is digitally displayed, as shown in FIG. 9B. FIG. 9B thus shows the display state in the recovery time measurement mode. In this manner, since the recovery time required to restore normal pulse count after jogging is measured and displayed, the jogger who runs a predetermined course every day or for every predetermined interval can determine the degree of improvement of his physical strength by checking the recovery rate after running along the predetermined course.

FIGS. 10 to 15 show another embodiment of the present invention. In the embodiment of FIGS. 1 to 9B, the improvement of physical strength is determined by measuring the time required for restoring the normal pulse count. However, the object of the present invention is achieved in the embodiment of FIGS. 10 to 15, by displaying the recovery rate to the normal pulse count.

Figure 10:
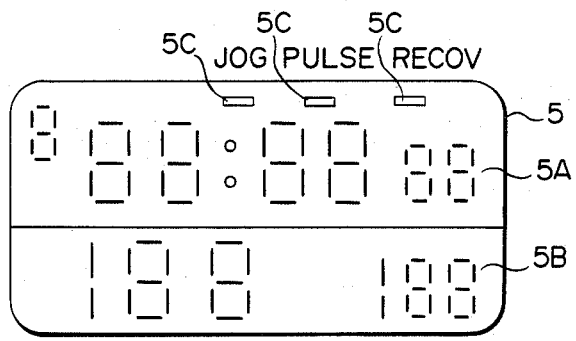
FIG. 10 is a plan view of a display unit used in another embodiment of the present invention.

FIG. 10 shows the segment electrode structure of display unit 5 in a jogging watch with a built-in pulse detection apparatus according to the present invention. The segment electrodes in unit 5 are constituted by liquid crystal display elements. Unit 5 includes upper and lower digital display sections 5A and 5B. The mode names, i.e., jogging mode name "JOG", pulse count mode name "PULSE", and recovery rate operation mode name "RECOV" are printed, and mode indicators 5C are arranged in the same manner as in display unit 5 in FIG. 2.

Switches SA, SB, S1, S2, and S3 are arranged on a watch case, as in FIG. 1. Fingerstall 2 with built-in pulse sensor 4 is connected to the case through cord 3. The operations of the switches and the circuit arrangement are the same as those shown in FIG. 4.

Figure 11:
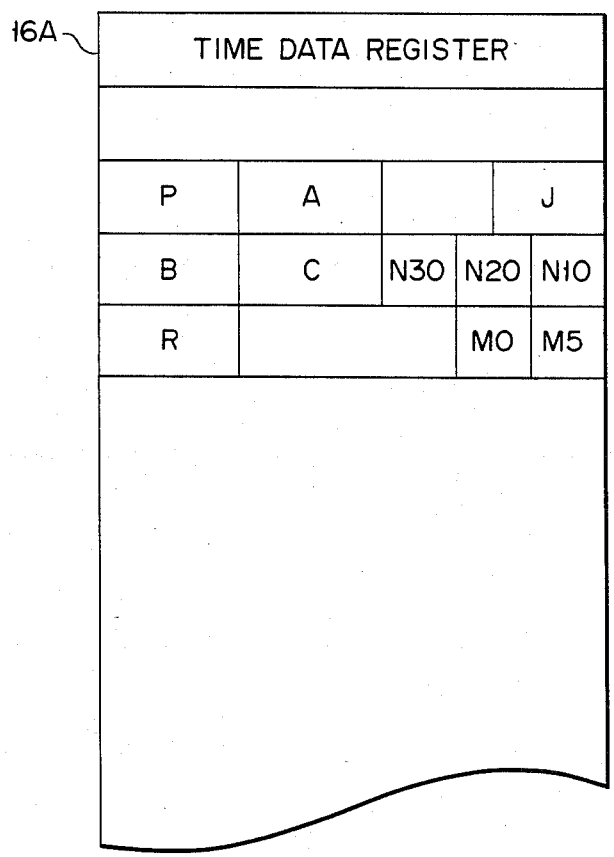
FIG. 11 is a memory map showing the detailed allocation of the memory area of a RAM used for the embodiment of FIG. 10.

The overall flow is the same as that in FIG. 6, except that the flow in step T6 (FIG. 6) differs from that in FIG. 8. The operation in step T6 is performed according to the flow chart in FIG. 12. RAM 16 has memory area allocation to perform the flow in FIG. 12, as shown in FIG. 11.

In addition to the P register for storing the pace count, the A register for storing the normal pulse count, and the J register for storing the jogging mode flag shown in FIG. 5, RAM 16 also includes an M0 register for storing a signal representing interruption of jogging, an M5 register for storing a signal representing the lapse of five minutes after jogging, a B register for storing the pulse count at the interruption of jogging, a C register for storing the pulse count five minutes after the interruption of jogging, N10, N20, and N30 registers for measuring times after the interruption of jogging, and an R register for storing the recovery rate.

Figure 12:
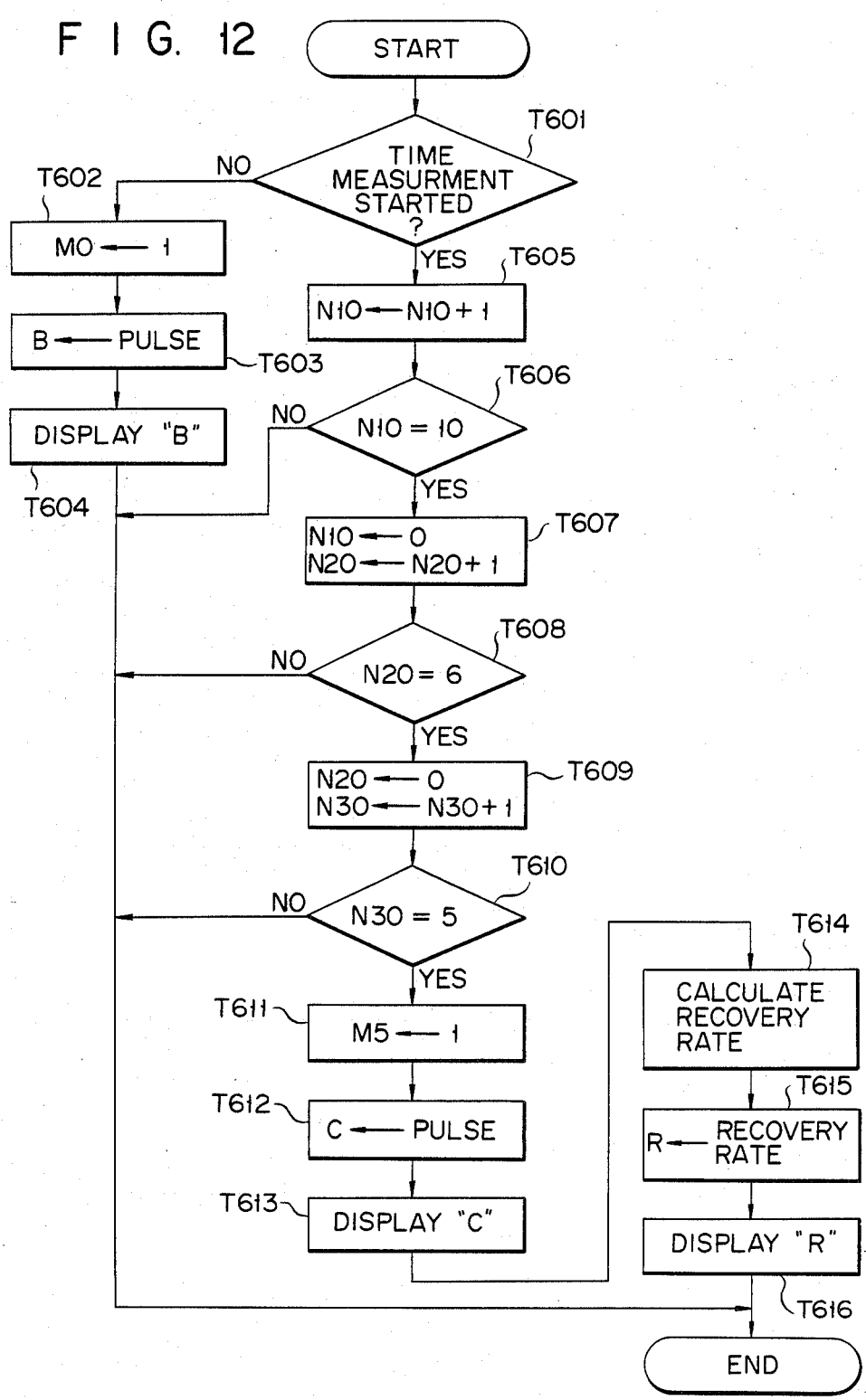
FIG. 12 is a flow chart for explaining pulse recovery rate calculation in the embodiment of FIG. 10.

Step T6 in FIG. 6 is processed as shown in FIG. 12. This flow is not started at the end of jogging time measurement. In step T601, it is determined whether a predetermined period of time has elapsed since the end of jogging. In this case, measurement is not started immediately after the end of jogging. The flow advances to step T602. A logic flag "1", representing the state immediately after the end of jogging, is set in the M0 register in RAM 16. The pulse count is measured immediately after the end of jogging, in step T603. The measured pulse count is transferred to the B register in RAM 16 and displayed on unit 5, in step T604. In this manner, the pulse count is measured and displayed as soon as the user stops jogging.

If time measurement has started after the end of jogging, this is detected in step T601, and the flow advances to step T605. The value of the N10 register for measuring one-second digits, among the N10 to N30 registers in RAM 16, is incremented by one. In step T606, it is determined whether the value of the N10 register is "10", i.e., whether 10 seconds have elapsed since the end of jogging. If YES in step T606, the content of the N10 register is cleared and the value of the N20 register for counting the 10-second digit is incremented by one, in step T607. In step T608, it is determined whether the value of the N20 register is "6", i.e., whether 60 seconds have elapsed since the end of jogging. If YES in step T608, the content of the N20 register is cleared, and the value of the N30 register for counting one-minute digits is incremented by one in step T609. Thereafter, in step T610, it is determined whether the value of the N30 register is "5", i.e., whether five minutes have elapsed since the end of jogging. If YES in step T610, the five-minute lapse flag "1" is set in the M5 register in RAM 16.

If five minutes have elapsed since the end of jogging, the flow advances to step T612, to detect a pulse count. The pulse count five minutes after the end of jogging is transferred to the C register in RAM 16. The pulse count is then digitally displayed on unit 5, in step T613.

The flow advances to step T614 and the recovery rate of the pulse count is calculated as follows:

$$[1-(C-A)/(B-A)] \times 100 = \text{Recov (Recovery rate)}$$

Figure 14:
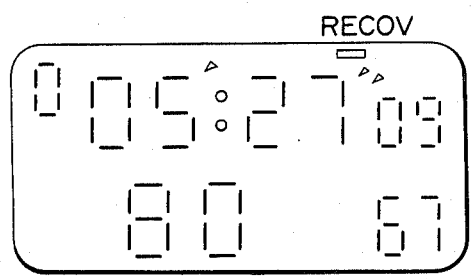

The recovery rate is calculated using the A register (normal pulse count), the B register (pulse count as soon as the user stops jogging), and the C register (pulse count five minutes after the end of jogging). The recovery rate is transferred to the R register in RAM 16, in step T615, and is digitally displayed on display unit 5, in step T616. FIG. 14 shows the display state of the results. In addition to displaying the time as soon as the user stops jogging, the pulse count "80", five minutes after the stop of jogging and the corresponding recovery rate of 67%, are digitally displayed. Since the user can determine his pulse count immediately after he has stopped jogging and five minutes thereafter, he can check if optimal exercise has been taken or how his physical strength has been improved.

Figure 13:
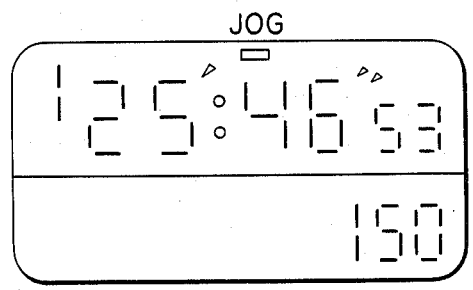
FIGS. 13, 14, and 15 are views showing details of the display unit in FIG. 10.
Figure 15:
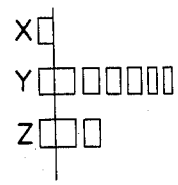

FIG. 13 shows a display state during jogging. Display section 5A displays the lapse time from the start of jogging, and display section 5B displays a preset pulse count. In the above embodiment, pulse counts immediately after the stop of jogging and five minutes thereafter are digitally displayed. However, as shown in FIG. 15, they may be displayed as a graph. Referring to FIG. 15, reference symbol X is the normal pulse count; Y, a pulse immediately after the end of jogging; and Z, a pulse five minutes after the end of jogging. These pulse counts can be displayed simultaneously on different display elements.

If the previously calculated recovery rate is stored and the increase/decrease of the current recovery rate to the previous recovery rate is displayed as a numeric value, a percentage, or an arrow, the degree of improvement of physical strength can be accurately checked.

In the above embodiment, a recovery rate of 100% is given upon recovery to the normal pulse count. However, the normal pulse count may be given as 100%. In this case, a percentage of the pulse count five minutes after the stop of jogging may be calculated using the normal pulse count as 100%. In this case, in step T614, $(C/A) \times 100$ is calculated. For example, if the normal pulse count is 70 and the measured pulse count is 80, $(80/70) \times 100 = 114\%$ (recovery rate).

In the above arrangement, the recovery rate is simply displayed. However, if the recovery rate is stored in a memory together with a date and the like, it can be displayed upon operation of a switch or the like. Therefore, for a person who does the same exercise every day, when the recovery rate for each day is stored, he can know the development of physical strength.

As shown in FIG. 1, in the above embodiment, the user inserts his finger into fingerstall 2 with pulse sensor 4, to measure his pulse count at any time. If a pulse sensor is arranged on a watch case, as shown in FIG. 16, pulse count measurement cannot be performed unless the user brings his finger into contact with the sensor.

Figure 4:
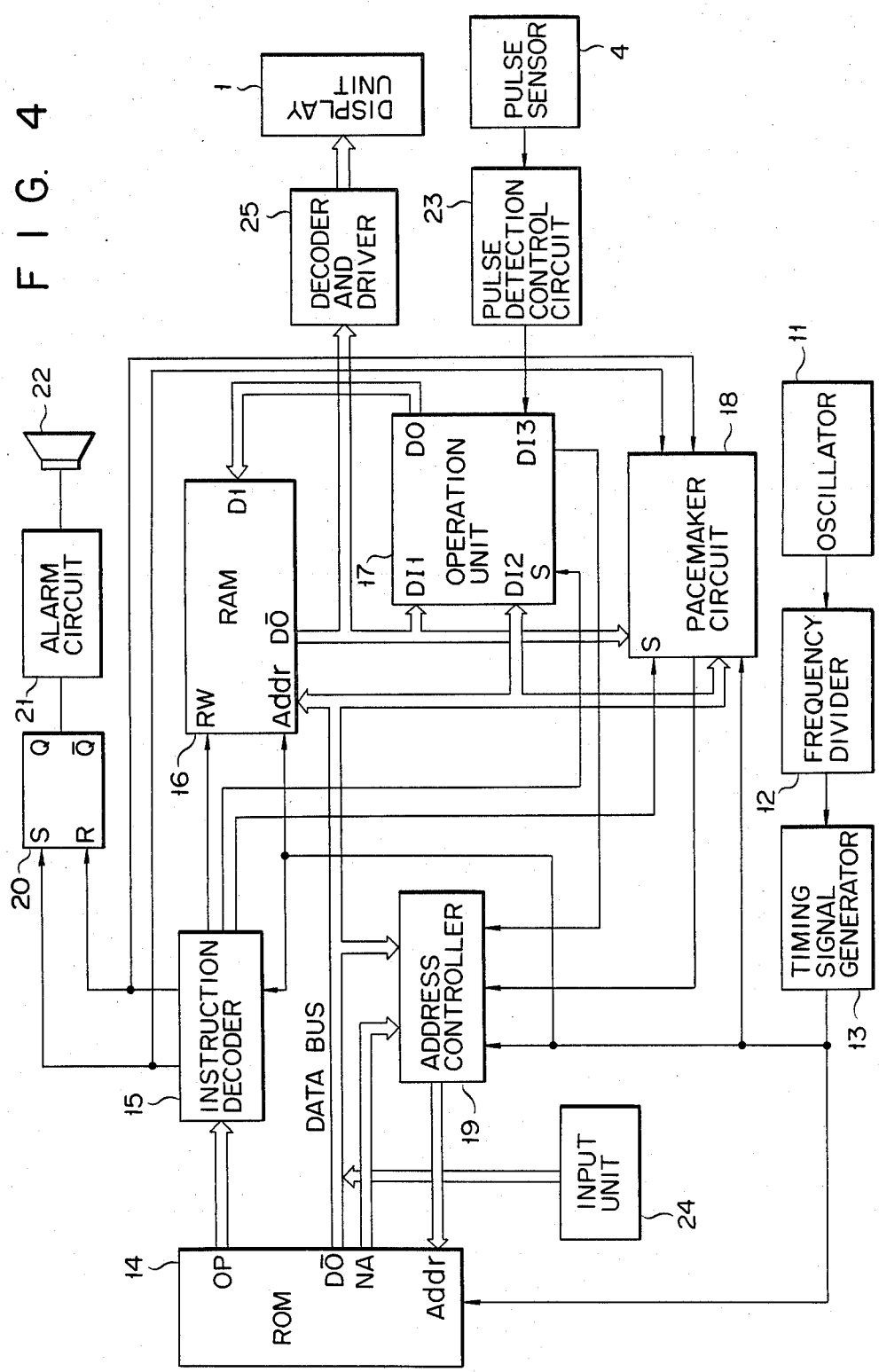
FIG. 4 is a block diagram of the jogging watch in FIG. 1.

If an operation for setting flip-flop 20 in FIG. 4 to cause alarm circuit 21 to generate an alarm tone is inserted between steps T610 and T611 in FIG. 12, the user will know five minutes have elapsed, through hearing the alarm tone. Then, if the user puts his finger into the sensor, his pulse count five minutes after the end of jogging can be measured.

When the alarm sound is generated after five minutes have elapsed, as described above, a memory for storing the normal pulse count or calculation of the recovery rate can be omitted, and the recovery rate can be confirmed by displaying the pulse count after five minutes. More specifically, if the user of the timepiece knows his pulse count, when the pulse count after the lapse of five minutes from the end of the exercise is displayed, he can calculate the recovery rate by himself.

FIGS. 16 to 23 show still another embodiment of the present invention, wherein a pulse sensor is mounted on a watch case, as described above.

FIG. 16 shows part of the front surface of wristwatch case 100. Display unit 102 is arranged on case 100, to display the date, day, pulse count, and the like. Pulse sensor 103 is also arranged on case 100. The user brings his finger into contact with sensor 103, to obtain his pulse count. Sensor 103 comprises LED 104 as a light-emitting element, phototransistor 105 as a light-receiving element, and metal electrodes 106a and 106b arranged outside LED 104 and phototransistor 105, respectively. Display unit 102 comprises liquid crystal display elements. Unit 102 includes seven day display sections 107 for displaying the day of the week or the magnitude of the pulse wave upon detection of the pulses, and 7-segment digital display section 108 for displaying time or a one-minute pulse count. Display section 108 displays the time, the pulse count, the recovery time required to restore the normal pulse count (FIGS. 1 to 9B), and the recovery rate (FIGS. 10 to 15).

Figure 18:
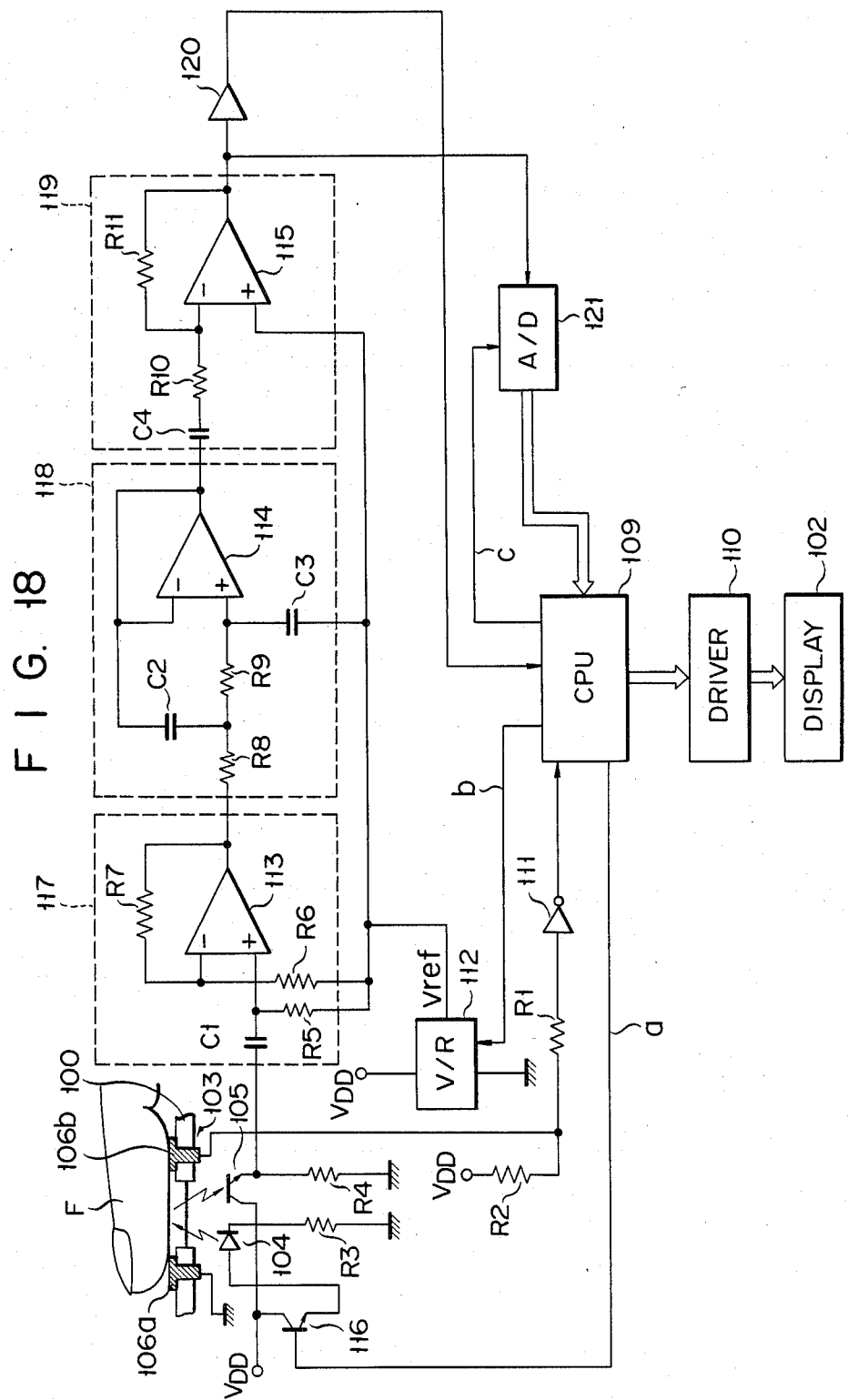
FIG. 18 is a diagram showing a jogging watch circuit in FIG. 16.

FIG. 18 is a circuit diagram showing a circuit including a pulse detector according to the present invention. Referring to FIG. 18, the circuits excluding pulse sensor 4 and pulse detection control circuit 23 (FIG. 4) are arranged in central processing unit (to be referred to as a CPU hereinafter) 109.

In pulse sensor 103 constituting the pulse detection apparatus, when the user places his finger on metal electrodes 106a and 106b, electrodes 106a and 106b are rendered conductive through the user's body. A low level signal (ground potential) from grounded electrode 106a is input to inverter 111 through electrode 106b and resistor R1. Inverter 111 normally receives a high level signal derived from the power source voltage (VDD) connected to resistor R2. An output signal from inverter 111 becomes high, so that a high level signal is input to CPU 109. CPU 109 outputs control signal b in response to the signal from inverter 111, to cause voltage regulator 112 to operate. Regulator 112 supplies drive voltage Vref to operational amplifiers 113 to 115 connected to its output.

Transistor 116 is turned on/off in response to control signal from CPU 109, so that a current flows in LED 104 and resistor R3 which are sequentially connected to the emitter of transistor 116, and LED 104 is turned on. Light from LED 104 is reflected by finger F, and the reflected light is incident on phototransistor 105. The emitter of phototransistor 105 is connected to resistor R4, and a current representing a change in light intensity in phototransistor 105 is input to sample/hold circuit 117. Circuit 117 comprises operational amplifier 113, capacitor C1, and resistors R5, R6, and R7. Sample/hold circuit 117 converts a pulse waveform (FIG. 19A) into a stepped continuous waveform (FIG. 19B). The continuous signal is then input to low-pass filter 118. Filter 118 comprises operational amplifier 114, capacitors C2 and C3, and resistors R8 and R9. Low-pass filter 118 eliminates a high-frequency ripple component included in the input waveform and supplies a signal having a waveform in FIG. 19C to AC amplifier circuit 119. Circuit 119 comprises operational amplifier 115, capacitor C4, and resistors R10 and R11. AC amplifier circuit 119 amplifies an input waveform and supplies an amplified result to Schmitt trigger circuit 120. Circuit 120 converts the input signal to a rectangular pulse signal, as shown in FIG. 19D. The pulse signal is then output to CPU 109. CPU 109 calculates the period (Pt) between the leading edges of two pulses of the output from schmitt trigger circuit 120, and repeats this operation whenever a pulse signal is supplied thereto. CPU 109 calculates an average value of the period data of three previous signals and converts the average value into a pulse count per minute (e.g., 60/[the average value of the period data]). The calculation result (the pulse count per minute) is displayed on display unit 102 through display driver 110. In period data average value calculation, whenever new period data is obtained, it is compared with three previous period data. If the new data falls within the old data, the oldest data is cleared, in order to calculate the average value of new three period data. However, if the new data falls outside the old data, the new data is cleared, in order to continue the display of the previous pulse count.

The output from the AC amplifier circuit 119 is also input to A/D (Analog/Digital) converter 121. Converter 121 converts the output from amplifier circuit 119 into digital outputs, in response to control signal c from CPU 109, and the digital outputs are input to CPU 109. The digital outputs are then transferred to display unit 102 through display driver 110, and the magnitude of the pulse wave is displayed as an analog value, using display section 107 in unit 102.

The pulse count detection operation will now be described with reference to FIGS. 20 to 23. When finger F is not placed on metal electrodes 106a and 106b, the input signal to inverter 111 is high, and therefore an output signal of low level is supplied to CPU 109. In this state, control signals a, b, and c are not output from CPU 109, and the pulse detection apparatus is kept disabled.

When finger F is placed on electrodes 106a and 106b, a high level signal is input to CPU 109 through inverter 111, thereby causing CPU 109 to output control signals a, b, and c. The pulse detection apparatus is then enabled. Voltage regulator 112 is operated in response to control signal b, to supply drive voltage Vref to operational amplifiers 113 to 115. Transistor 116 is turned on in response to control signal a, and LED 104 is turned on. Light from LED 104 is incident on finger F, and the reflected light corresponding to a change in blood flow caused by pulses is incident on phototransistor 105. Phototransistor 105 outputs a signal corresponding to the amount of light received thereby. This signal is converted by sample/hold circuit 117 to a stepped continuous signal. The high-frequency ripple component is removed from the signal by low-pass filter 118. The output from filter 118 is amplified by amplifier circuit 119, and the amplified signal is input to A/D converter 121.

FIG. 20 shows the waveform of an output from amplifier circuit 119. The waveform in FIG. 20 is obtained when the finger is properly placed on the sensor portion and the pulses are detected in an environment where ambient brightness and temperature are suitable for pulse measurement. If the detection state is good, the amplitude of the signal having the waveform in FIG. 20 is greatly changed. This pulse signal is input to converter 121 and converted to a digital signal in synchronism with sampling timings t1 to t6 under the control of CPU 109. Peak value data signals obtained at timings t1 to t6 are displayed on display section 107 in unit 102. FIGS. 21A to 21F show display states corresponding to the waveform in FIG. 20. The peak values obtained at timings t1 to t6 are displayed as a bar graph on display section 107. In this case, the lengths of bars are changed corresponding to the peak values. If the detection state is good, as shown in FIG. 2, and the amplitude of the waveform of the output from amplifier circuit 119 is greatly changed, the bar graph display is accordingly greatly changed.

Figures 21A, 21B, 21C, 21D, 21E, 21F, 22:
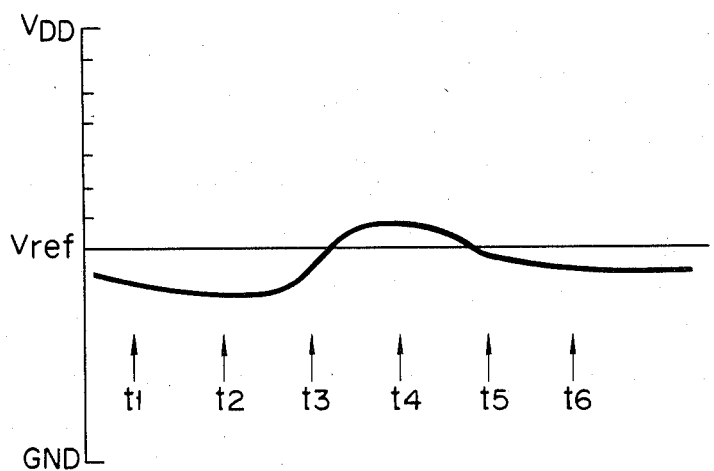

FIG. 22 shows the waveform of an output from amplifier circuit 119 when the detection state is poor. More specifically, the finger is not properly placed on the sensor portion, or pulse measurement is performed in an improper environment. If the detection state is poor, the amplitude of the resultant signal is small, as shown in FIG. 22. Therefore, changes in the bar graph display are small, as shown in FIGS. 23A to 23F.

Since the changes in the bar graph display change according to the detection state, the user must check the display contents, and change his finger contact position or measure his pulses n a bright place. Then, the detection state can be improved, to obtain measured values (pulse counts) with high precision.

Figure 24:
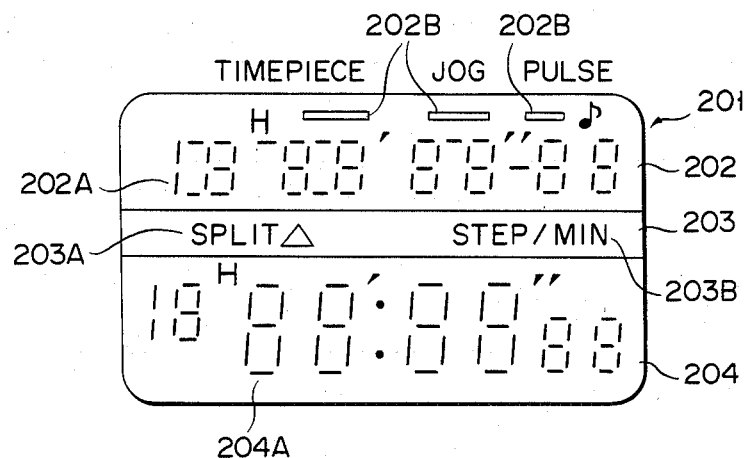
FIG. 24 is a plan view showing a display unit according to still another embodiment of the present invention.

FIGS. 24 to 29 show still another embodiment of step T4 (shown in FIG. 7 in detail) in FIG. 6. In this embodiment, the watch case, the switch, and the sensor are the same as those in FIG. 1. The overall circuit is the same as that in FIG. 4. The flow chart of the operation of the circuit is the same as that in FIG. 6. Display unit 201 comprises liquid crystal display elements of a segment electrode structure and is divided into upper, middle, and lower display sections, as shown in FIG. 24. Upper display section 202 consists of digital display portion 202A for digitally displaying hour, minute, second, and second/100, and mode indicators 202B arranged in correspondence with the printed mode names, i.e., timepiece mode name "TIMEPIECE", jogging mode name "JOG", and preset maximum/minimum pulse count setting mode "PULSE". Middle display section 203 consists of "SPLITΔ" display portion 203A for indicating that the displayed time is a split time, and "STEP/MIN" display portion 203B for indicating that the displayed content on lower display section 204 is the jogging pace (steps/minute). Lower display section 204 includes display portion 204A for digitally displaying the hour, minute, second, and second/100.

Figure 25:
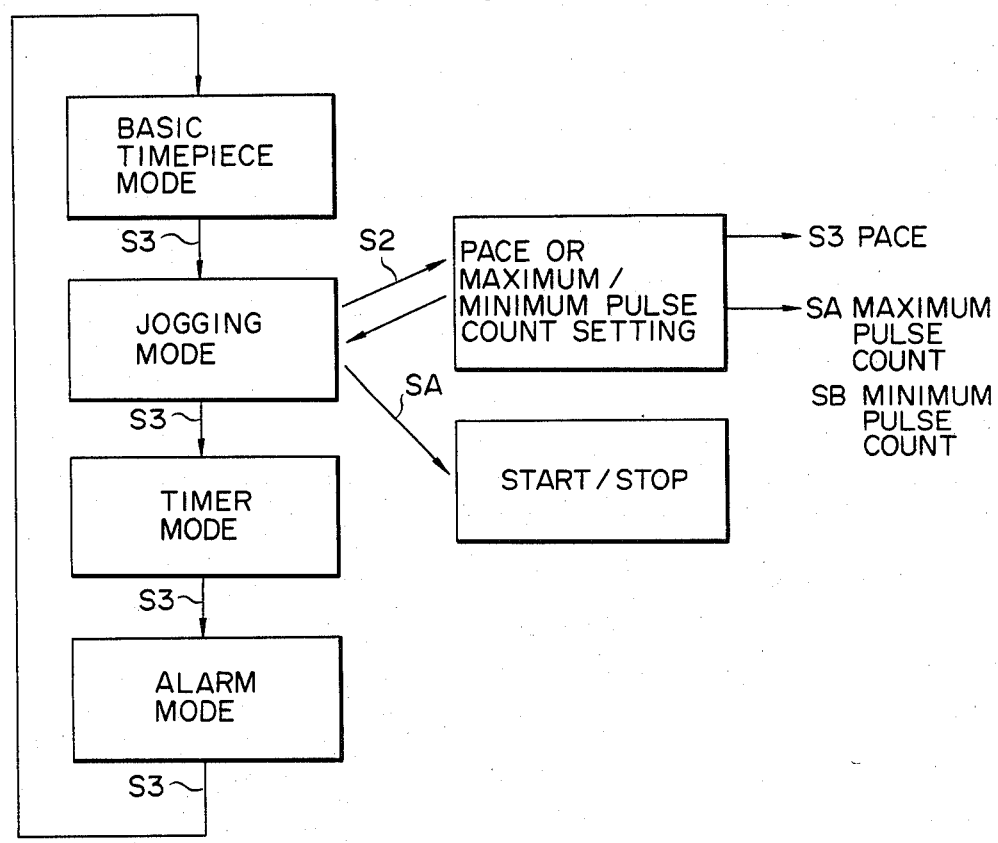
FIG. 25 is a flow chart showing changes in display modes upon switching operations.

As shown in FIG. 1, pushbutton switches SA, SB, S1, S2, and S3 are arranged on the upper surface and the side surfaces of the watch case. These switches function as shown in FIG. 25. More specifically, switch S3 serves as a mode selection switch for cyclically selecting the basic timepiece mode, the jogging mode, the timer mode, and the alarm mode. Switch S2 serves as a set mode selection switch for selecting jogging pace count setting or maximum/minimum pulse count setting. Upon operation of switch S2 in the setting mode, the currently set mode is cancelled, to restore the previous jogging mode. In addition, although omitted in FIG. 25, upon operation of switch S2 in the basic timepiece mode, the time correction mode is set. Upon operation of switch S2 in the alarm mode, the alarm setting mode is set. Upon operation of switch S3 in the pace count or maximum/minimum count setting mode, a desired pace count (steps/minute) can be set according to the number of operations of switch S3. A desired maximum pulse count is set according to the number of operations of switch SA. A desired minimum pulse count is set according to the number of operations of switch SB. In the jogging mode, switch SA serves as a start/stop switch, and switch SB serves as a split/reset switch.

Figure 26:
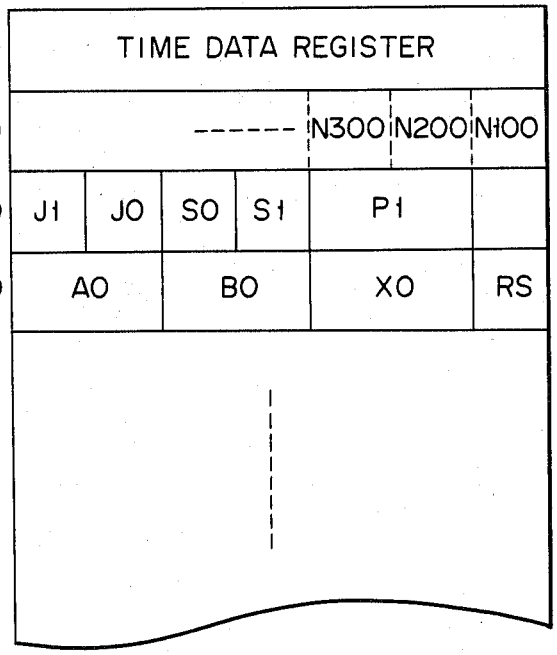
FIG. 26 is a memory map of the memory area of a RAM used in the embodiment of FIG. 24.

FIG. 26 shows a memory map of a RAM 16. RAM 16 has a user memory area in addition to the memory areas for timepiece data and system control data. A basic timepiece storage register is allocated in first line M100 of RAM 16. Jogging time measuring registers N300, N200, N100, . . . are allocated in second line M200. The N100 register is a register for a one-second digit, the N200 register is a register for a 10-second digit, and the N300 register is a register for a 1-minute digit. J1, J0, S0, S1, and P1 registers for jogging are allocated in third line M300 of RAM 16. A jogging mode flag is set in the J1 register. A start flag is set in the J0 register. A flag representing the lapse of one minute from the start of jogging is set in the S0 register. A 10-minute lapse flag is then set in the S1 register. A jogging pace count is set in the P1 register. The A0, B0, X0, and RS registers are allocated in fourth line M400 of ROM 16. The A0 register stores a maximum preset pulse count. The B0 register stores a minimum preset pulse count. The X0 register stores the measured pulse count. The RS register stores an alarm tone flag for indicating that the measured pulse count falls outside the range between the maximum and minimum pulse counts. In addition, alarm time data and timer count data are stored in RAM 16.

FIG. 27B shows a display state when the pace count is set, and FIG. 27C shows a display state when the maximum pulse count is set. In FIG. 27B, the pace count is set as "145 steps per minute". In FIG. 27C, the maximum pulse count is set as "180". The user can set a desired count by checking the displayed result. Referring to FIGS. 27B and 27C, mark "S" is displayed at the right end of upper display section 202. The minimum pulse count can be displayed, as shown in FIG. 27C. The user can set a desired value while observing the displayed content. FIG. 27A shows the display contents after the start of jogging. The split time is displayed in upper display section 202. "SPLITΔ" representing the displayed content of section 202 is displayed in middle display section 203. The lapse after the start of jogging is displayed in lower display section 204.

Figure 28:
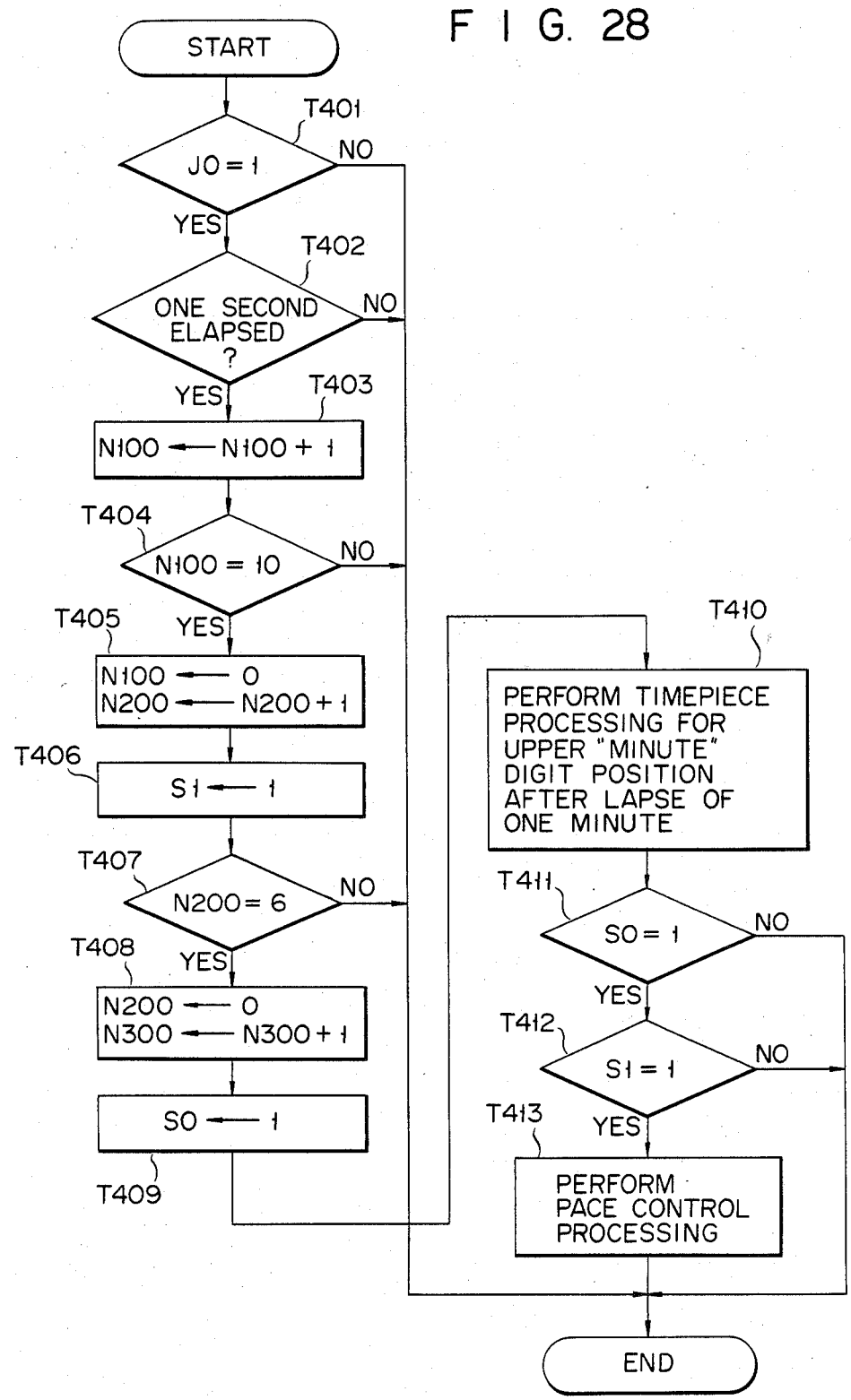
FIG. 28 is a flow chart for explaining the operation in the jogging mode.

FIG. 28 is a flow chart for explaining the detailed contents of still another embodiment, different from that in FIG. 7, for jogging processing in step T4 (FIG. 6).

In step T401, it is determined whether the start flag "1" is set in the J0 register. If switch SA is operated in the jogging mode and the user starts jogging, start flag "1" is set in the J0 register. The subsequent jogging processing is performed. However, if start flag "1" is determined not to have been set, no jogging processing is performed. In step T402, it is determined whether one second has elapsed after the start of jogging. If YES in step T402, the value of the N100 register (i.e., the register for counting the jogging time in units of seconds) is incremented by one, in step T403. If the value of the N100 register is "10", in step T404, i.e., if 10 seconds have elapsed since the start of jogging, the flow advances to step T405. In step T405, the N100 register is cleared, and at the same time the value of the N200 register (the register for measuring the jogging time in units of 10 seconds) is incremented by one. In step T406, the 10-second lapse flag "1" is set in the S1 register, to indicate that 10 seconds have elapsed since the start of jogging. Thereafter, it is determined, in step T407, whether the value of the N200 register is "6"; in other words, whether 60 seconds have elapsed. If YES in step T407, the flow advances to step T408. In this step, the content of the N200 register is cleared, and at the same time, the value of the N300 register (the register for counting the jogging time in units of minutes) is incremented by one. The one-minute lapse flag "1" is set in the S0 register in step T409, to indicate that 60 seconds have elapsed after the start of jogging.

The values of the N100, N200, and N300 registers are updated upon start of jogging, to sequentially measure 1- and 10-second digits and 1-minute digit. In step T410, the time measurement for the upper "minute" digit position after the lapse of one minute, is detected in the same manner as described above. In step T411, it is determined whether the one-minute lapse flag is set in the S0 register. If YES in step T411, it is determined, in step T412, whether the 10-second lapse flag of logic "1" is set in the S1 register. If YES in step T412, pace control processing (step T413) is performed. Pace control processing is performed at every interval of 10 seconds following the lapse of one minute from the start of jogging. Pace control processing is performed after the running pace is stabilized, since the pace is not stable when jogging has just started.

Figure 29:
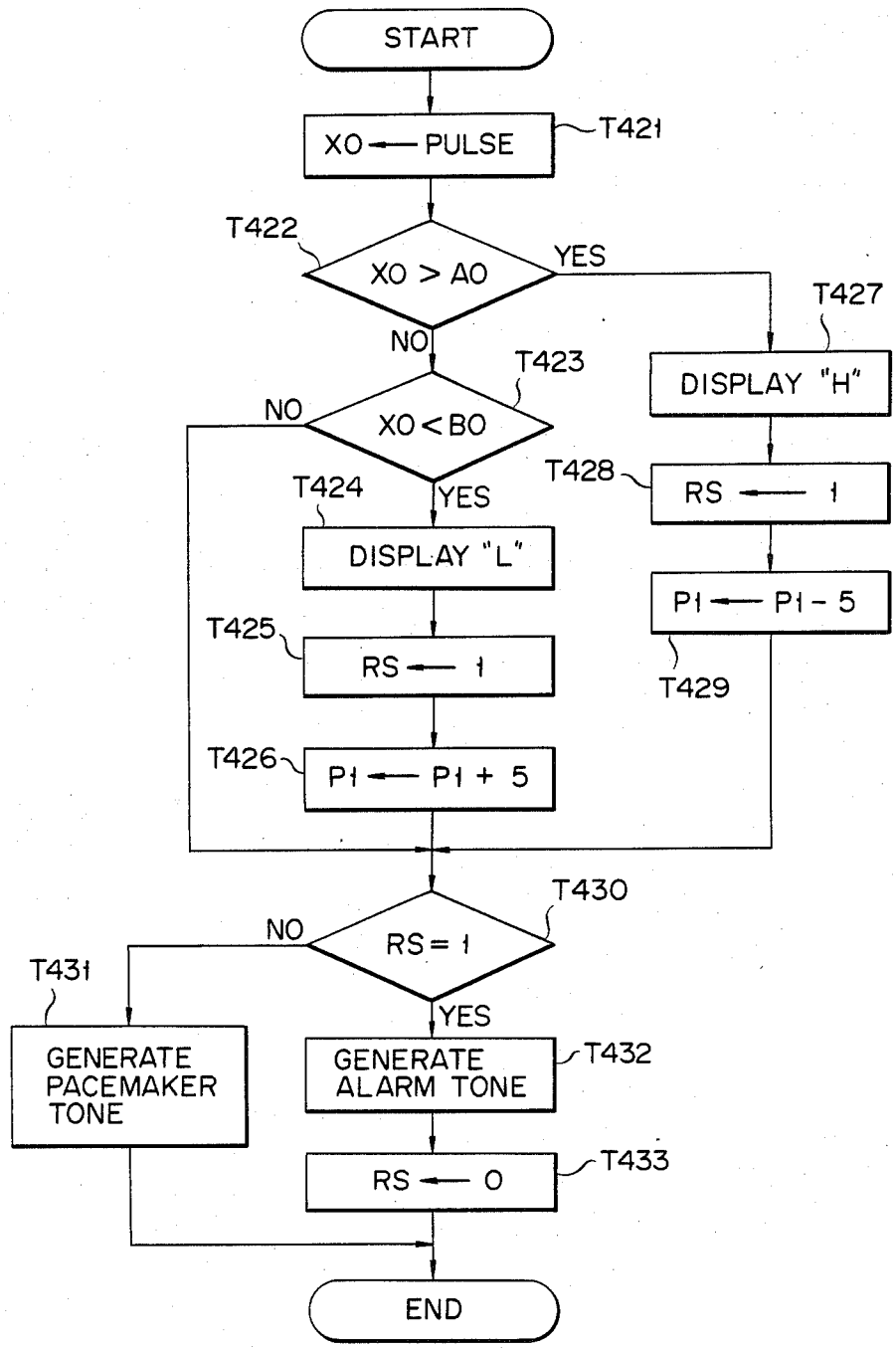
FIG. 29 is a detailed flow chart showing pace control processing in FIG. 28.

FIG. 29 is a flow chart for explaining the detailed contents of pace control processing (step T413). In step T421, the photoelectric pulse wave detected by the pulse sensor is converted to a signal corresponding to the pulses, and the converted signal is supplied to the operation section. The pulse count is set in the X0 register in RAM 16. In step T422, the maximum pulse count is compared with the measured pulse count transferred to the X0 register. If the measured pulse count is smaller than the maximum pulse count, the flow advances to step T423. The measured pulse count is compared with the minimum pulse count preset in the B0 register. If the measured pulse count is larger than the minimum pulse count, the flow advances to step T430. In step T430, it is determined whether the alarm tone processing flag is set in the RS register. The alarm tone processing flag "1" is set in the RS register when the measured pulse count falls outside the range between the maximum and minimum counts. As alarm tone processing is not performed, pace maker tone processing is performed, in step T431. In this processing, the pace tones are generated according to the pace count preset in the P1 register in RAM 16.

If the measured pulse count falls outside the range between the maximum and minimum pulse counts, for example, if the measured count exceeds the maximum count, this is detected in step T422, the flow advances to T427, where alarming (i.e. the measured count is excessively large) is performed, as indicated in FIG. 27D. If the maximum pulse count is preset by the user to be "180", as shown in FIG. 27, then, when the measured pulse count becomes "185", mark "H" is displayed at the right edge of upper display section 202. After the alarm display is completed, the flow advances to step T428. The alarm tone processing flag "1" is set in the RS register, and "5" is decremented from the value of the P1 register (step T429). The flow advances to step T430, to check the content of the RS register. Since "1" is set in the RS register, the flow advances to step T432 and alarm tone processing is then performed. Thereafter, in step T433, the content of the RS register is cleared. In this manner, when the measured count is larger than the maximum count preset by the user, the pace count "5", i.e., five steps/minute, in the P1 register is decremented, and at the same time the alarm tone is generated. The jogger can then change his pace in response to the alarm tone. When the measured pulse count is lower than the maximum, the pace tones are generated according to the reduced pace count, in step T431.

If the measured count is lower than the minimum pulse count preset by the user, this is detected in step T423 and the flow advances to step T424, where alarming (i.e. the measured pulse count is excessively low) is performed. In this case, mark "L" is displayed. The alarm tone processing flag "1" is set in the RS register in step T425, and "5" is added to the value of the P1 register, in step T426. In step T 430, the content of the RS register is checked. Since "1" is set in the RS register, alarm tone processing (in step T432) and clearing processing of the RS register (in stp T433) are sequentially performed. Even if the measured pulse count is smaller than the minimum count preset by the user, five steps/minute are added to the pace count in the P1 register, and at the same time the alarm tone is generated. The user can then change his jogging pace in response to the alarm. If the measured pulse count exceeds the minimum pulse count, the pace tones are generated, in step T431, according to the increased pace count.

In the above embodiments, jogging is exemplified. However, the present invention is also applicable to other types of exercise or training programs. In this case, the degree of improvement of physical strength can be similarly determined using the pulse detection apparatus.

In the above embodiments, the pulse count and the recovery rate are displayed on a liquid crystal display device. However, these can be printed out at a printer or the like. In particular, a jogger who runs along a predetermined course every day or at predetermined intervals can find out the improvement in his physical strength and physical condition by printing out the pulse counts and recovery rates after running along the course.

In the above embodiments, pulse is detected according to the change in blood flow at the finger tip. However, the pulse count may be detected by a pressure sensor. Alternatively, a sensor can be attached to a jogger's chest, to detect his pulse.

Furthermore, the pulse detection apparatus may be built into a compact calculator, an IC card, and the like, as well as in a wristwatch. The pulse detection apparatus may be used as a single unit.

What is claimed is:

1. A pulse detection apparatus comprising:
   key input means for inputting a pulse count per unit time;
   storage means for storing the pulse count which is input from said key input means;
   a pulse sensor for detecting an actual pulse;
   pulse measuring means for obtaining a pulse count per unit time responsive to a detection output signal from said pulse sensor;
   percentage calculating means for performing a percentage calculation using the pulse count obtained by said pulse measuring means and the pulse count stored in said storage means, and for obtaining percentage data based on the pulse count stored in said storage means; and
   display means coupled to the output of said percentage calculating means for displaying, in terms of percentage, the result of calculation obtained by said percentage calculating means.

2. An apparatus according to claim 1, wherein said pulse measuring means comprises a timer circuit for counting a predetermined frequency signal, and the pulse count for measuring responsive to a signal from said pulse sensor when the value of said timer circuit reaches a predetermined value.

3. An apparatus according to claim 2, wherein said timer circuit comprises alarm tone generating means for generating an alarm tone when the value of said timer circuit reaches the predetermined value.

4. An apparatus according to claim 1, wherein the pulse count input at said key input means and stored in said storage means is the pulse count per minute.

5. An apparatus according to claim 1, wherein said percentage calculating means includes means for dividing the pulse count, which is obtained by said pulse measuring means, by the pulse count stored in said storage means, and for providing a result of such diversion in terms of percentage.

6. An apparatus according to claim 1, wherein said pulse sensor comprises a light-emitting element and a light-receiving element, for receiving reflected light representing a change in blood flow caused by a change in the pulse rate.

7. An apparatus according to claim 1, wherein said pulse sensor comprises a light-emitting element, a light-receiving element means for receiving reflected light representing a change in blood flow caused by a change in the pulse rate, and an amplifier circuit means for receiving a signal from said light-receiving element, and said display means comprises amplitude display means for displaying the amplitude of a waveform of an output from said amplifier circuit.

8. An apparatus according to claim 7, wherein said amplitude display means comprises a plurality of dot display elements.

9. An apparatus according to claim 1, wherein said pulse sensor comprises touch-detecting means for detecting that a finger has been brought into contact therewith, and said pulse measuring means starts pulse measurement according to a detection signal from said touch detecting means.

10. A pulse detection apparatus comprising:
    key input means for inputting a pulse count per unit time;
    pulse count storage means for storing the pulse count which is input from said key input means;
    a pulse sensor for detecting an actual pulse;
    time measuring means for measuring a frequency signal of a predetermined time period;
    a start/stop switch for controlling a measuring operation of said frequency signal by said time measuring means and for measuring an exercise time;

timer means for measuring a lapse time following a stop operation carried out by said start/stop switch;

pulse measuring means for obtaining a pulse count per unit time in response to a detection signal from said pulse sensor when the lapse time measured by said timer means reaches a predetermined value;

recovery data calculating means for calculating, in terms of percentage, recovery data associated with a recovery of a user to a condition of a normal pulse count from the pulse count obtained by said pulse measuring means and the pulse count stored in said pulse count storage means; and display means for displaying, in terms of percentage, the recovery data obtained by said recovery data calculating means.

11. An apparatus according to claim 10, wherein said pulse sensor comprises a light-emitting element, and a light-receiving element for receiving reflected light representing a change in blood flow caused by a change in the pulse rate.

12. An apparatus according to claim 10, wherein said pulse sensor comprises a light-emitting element, a light-receiving element means for receiving reflected light representing a change in blood flow caused by a change in the pulse rate, and an amplifier circuit means for receiving a signal from said light-receiving element, and said display means comprises amplitude display means for displaying the amplitude of a waveform of an output from said amplifier circuit.

13. An apparatus according to claim 12, wherein said amplitude display means comprises a plurality of dot display elements.

14. An apparatus according to claim 10, wherein said pulse sensor comprises touch-detecting means for detecting that a finger has been brought into contact therewith, and said pulse measuring means starts pulse measurement according to a detection signal from said touch-detecting means.

15. An apparatus according to claim 10, wherein said pulse measuring means comprises means for generating an alarm tone when the elapsed time measured by said timer means reaches a predetermined value, and the pulse count is measured according to a detection signal from said pulse sensor after the alarm tone has been generated.

16. An apparatus according to claim 10, wherein the recovery data obtained by said recovery data calculating means represents percentage data obtained by dividing the difference between that pulse count when the timer means reaches said predetermined value and the pulse count stored in said pulse count storage means by the difference between the pulse count stored in said pulse count storage means and the pulse count occurring immediately after an exercise has been finished.

17. An apparatus according to claim 10, further comprising stop timing pulse count detecting means for detecting a pulse count at a stop timing by said start/stop switch, and wherein said recovery data calculating means comprises percentage operating means for calculating the percentage difference between the pulse count obtained by said stop timing pulse count detecting means and that stored in said pulse count storage means, and the difference between the pulse count obtained from said pulse measuring means and the pulse count stored in said pulse count storage means.

18. An apparatus according to claim 10, wherein said recovery data calculating means comprises comparing means for comparing the pulse count obtained from said pulse measuring means and that stored in said pulse count storage means, the lapse time of said timer means being displayed on said display means when said comparing means detects that the pulse count measured by said pulse count measuring means is smaller than the count stored in said pulse count storage means.

19. An apparatus according to claim 10, wherein said time measuring means further comprises pace tone generating means for generating a pace tone for every predetermined interval.

20. An apparatus according to claim 10, further comprising maximum pulse count storage means for storing a maximum pulse count higher than that stored in said pulse count storage means, pace tone generating means for generating a pace tone during measurement by said time measuring means, in-measurement pulse measuring means for causing said pulse measuring means to count the pulse count during measurement by said time measuring means, detecting means for detecting whether the pulse count measured by said in-measurement pulse measuring means is larger than the maximum pulse count stored in said maximum pulse count storage means, and pace tone control means for changing the pace tone generated by said pace tone generating means on the basis of a detection result of said detecting means.

21. An apparatus according to claim 10, further comprising minimum pulse count storage means for storing a minimum pulse count lower than the count stored in said pulse count storage means, pace tone generating means for generating a pace tone during measurement by said time measuring means, detecting means for detecting whether the pulse count measured by said in-measurement pulse measuring means is smaller than the minimum pulse count stored in said minimum pulse count storage means, and pace tone control means for changing the pace tone generated by said pace tone generating means on the basis of a detection result of said detecting means.

* * * * *